United States Patent [19]

Bremer

[11] Patent Number: 5,042,462
[45] Date of Patent: Aug. 27, 1991

[54] CERVICAL TRACTION TONGS

[76] Inventor: Paul W. Bremer, 4801 Dawin Rd., Jacksonville, Fla. 32207

[21] Appl. No.: 605,422

[22] Filed: Oct. 30, 1990

[51] Int. Cl.⁵ .................. A61H 1/02; A61F 5/04; F16B 25/00
[52] U.S. Cl. ................................. 128/75; 606/130; 411/386
[58] Field of Search ............... 128/75, 76 R, 84 R, 128/84 C, 87 B, 87 R; 606/118, 120, 130, 139; 411/386

[56] References Cited

U.S. PATENT DOCUMENTS

| | | | |
|---|---|---|---|
| 3,401,688 | 9/1968 | Crutchfield | 128/84 R |
| 3,604,412 | 9/1971 | Gardner | 128/75 |
| 3,654,923 | 4/1972 | Crutchfield | 128/84 R |
| 3,923,046 | 12/1975 | Heifetz | 128/75 |
| 4,444,179 | 4/1984 | Trippi | 128/75 |
| 4,539,979 | 9/1985 | Bremer | 128/75 |
| 4,612,930 | 9/1986 | Bremer | 606/130 |
| 4,667,660 | 5/1987 | Eingorn | 128/75 |
| 4,883,264 | 6/1989 | Bremer | 128/75 |

Primary Examiner—Robert A. Hafer
Assistant Examiner—Michael Brown
Attorney, Agent, or Firm—Nixon & Vanderhye

[57] ABSTRACT

Cervical traction tongs having cooperating first and second curved arms made of MRI and biologically compatible and CT transparent material. Skull pins having main bodies of MRI and biologically compatible and CT transparent material, and pointed skull engaging tips of radiolucent material (e.g. single crystal alumina ceramic) extend through openings at one end of the arms, while at the other ends the arms are connected together in an adjustable manner, so as to adjust the spacing between the pin pointed tips. The arms have enlarged circular end terminations having radially extending serrations which cooperate together, and are held in a position to which they are moved by a through extending bolt and nut. The arms have sufficient elasticity to provide constant pressure urging the pointed pin tips against the human skull during use. A flexible strand for applying tension is passed through an arcuate elongated opening in the serrated end terminations of the arms. Torque limiting caps associated with the pins apply torque. When used to treat a human with an injury to the cervical spine, the tongs and skull pins are removed from sterile packaging, and once the human need no longer remain in traction, the tongs are disposed of.

20 Claims, 2 Drawing Sheets

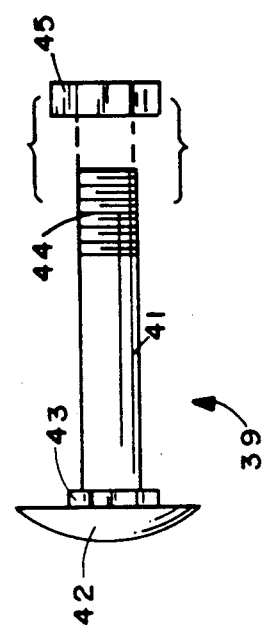
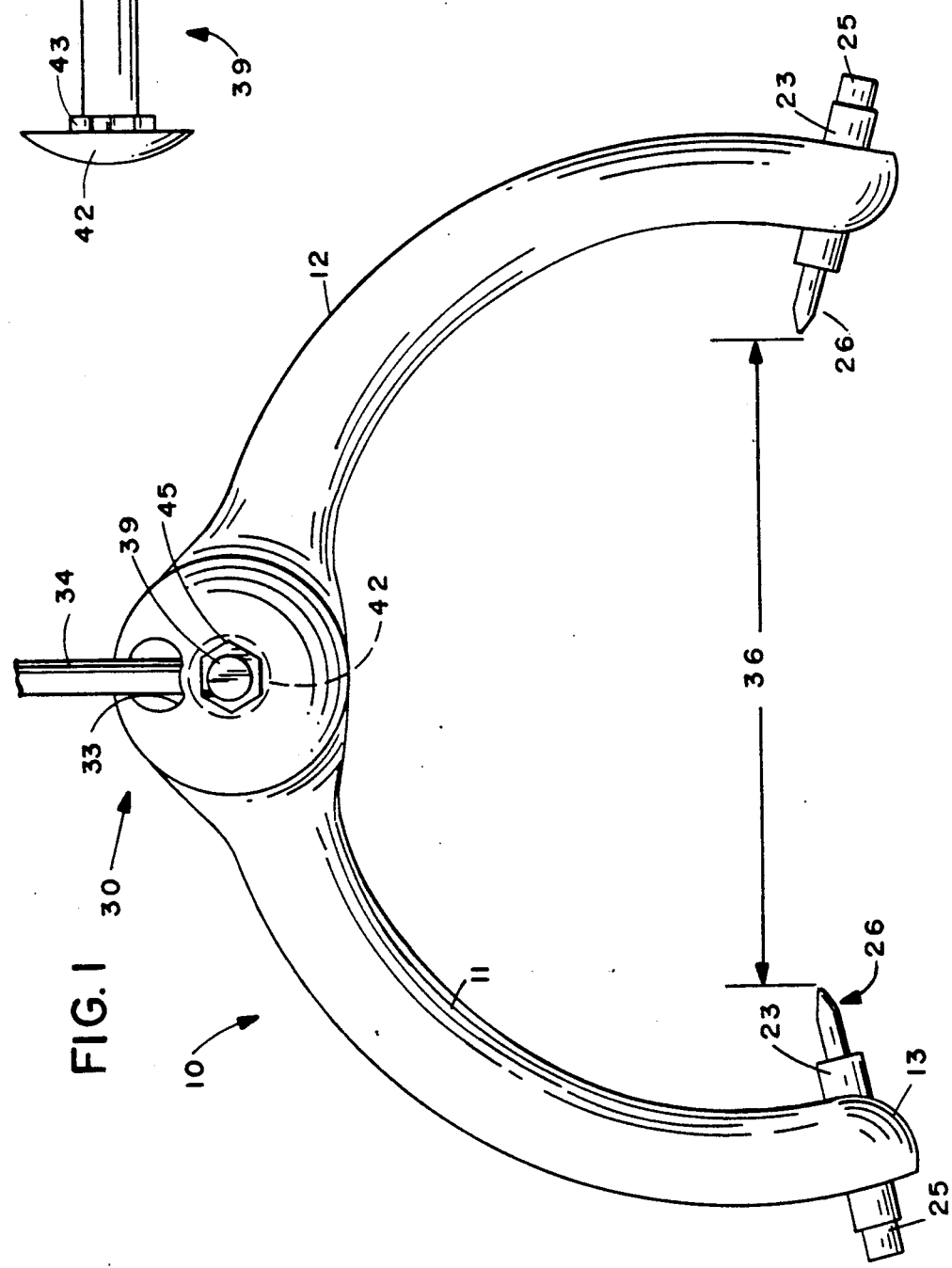

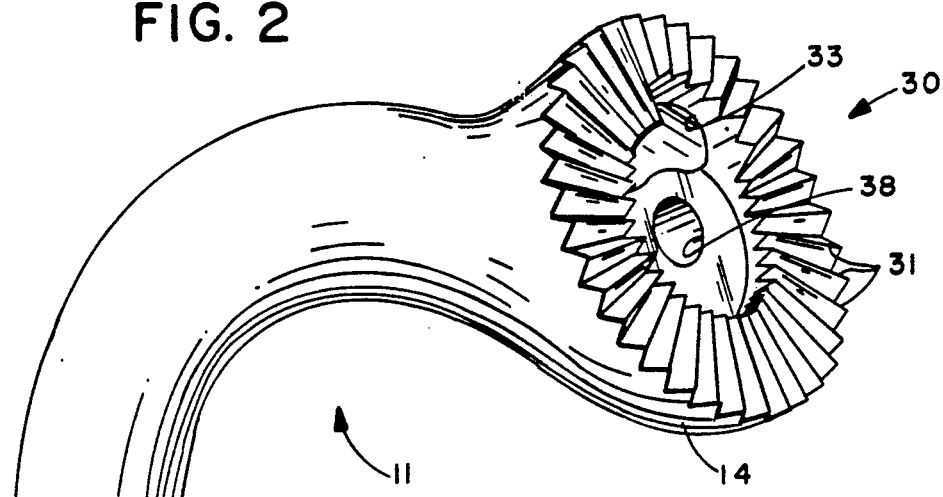
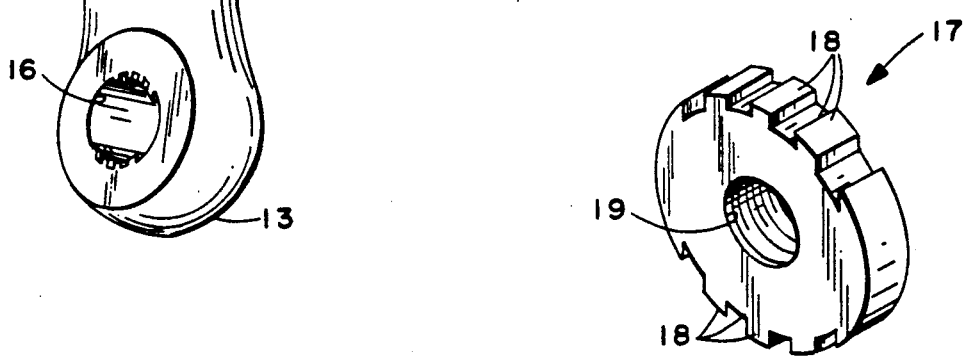
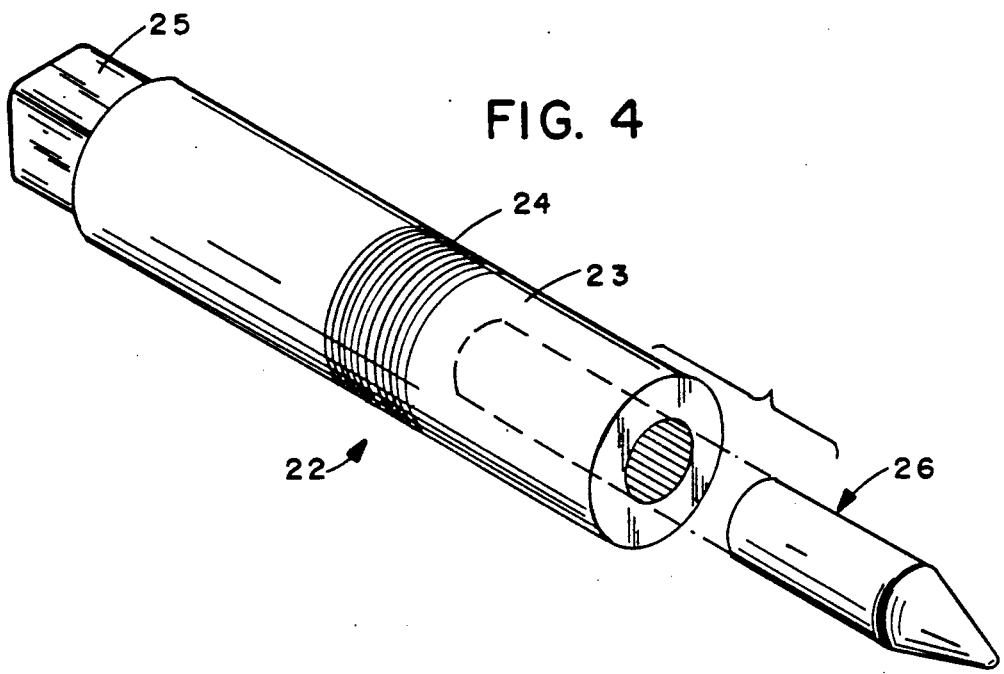

CERVICAL TRACTION TONGS

BACKGROUND AND SUMMARY OF THE INVENTION

For decades, fractures and dislocations of the cervical spine have been treated by applying cervical traction. Traction is applied utilizing tongs which typically have spring loaded pins that penetrate the skin and engage the outer table of the skull of the patient, a strand connected to the tongs applying the necessary traction force. Sometimes the tongs are articulated, such as shown U.S. Pat. No. 3,401,688, to apply a clamping force with the pins rather than spring loading of the pins.

Most existing tongs and related components are made of stainless steel. Because of that, the tong systems blocks CT scans of the brain, and also interfere with MRI scanning of the brain, although the MRI interference may be solved by using titanium as the material of the tong and pins. Obtaining clear images of the brain, especially CT scans, is very important for most patients with cervical injuries since the mechanism of injury that causes the cervical distress is usually a blow to the head, which can also cause brain injury. Using traditional tongs, a neurosurgeon or orthopedic surgeon must go with the patient to radiology and remove the tongs while the patient is having a scan, then reapply them. This is time consuming for the physician and dangerous for the patient. The other alternative is to delay stabilizing the patient with tongs until CT scans can be obtained, which is even more dangerous to the patient.

According to the present invention, cervical traction tongs are made of a material which is entirely MRI and biologically compatible, and CT transparent. Only the pointed pin tips are not completely CT transparent, and those pin tips are radiolucent, so that they result in minimal artifact (about equal to that of bone) in resultant film so that there is no interference with diagnosis. Preferably the pins are made of single crystal alumina ceramic, such as shown in U.S. Pat. No. 4,612,930, the disclosure of which is hereby incorporated by reference herein.

The typical materials of which the tongs and skull pins can be made are a wide variety of MRI compatible and CT transparent plastics. The plastic must have sufficient elasticity, however, so that the arms of the tongs can apply constant pressure of the pin points against skull bone. There are a wide variety of materials that can be used for this purpose, some examples of which are: glass filled (e.g. 35%) ULTEM (a trademark of General Electric) polyesteramide, or glass or carbon fiber filled polysulfone, or fiber reinforced tempered nylon.

While the tongs according to the invention solve the problem of interference with brain scans and the like, because plastic—of which the pin bodies are made—is not as strong as the conventional pin and tong materials such as stainless steel and titanium, it is necessary to provide adjustability of the width of the tongs; that is the spacing between the pointed tips of the pins must be adjustable. This is accomplished by providing the tongs as interconnected first and second arms, one being a mirror image of the other. At a first end of the arms they have means for receipt of the bodies of the pins so that the pins extend through the arms with the tips pointing toward each other. At the second ends of the arms they have cooperating structures which allow the relative angular position of the arms to be adjusted, yet allowing the arms to be positively held in place in the position to which they have been adjusted, so that the spacing between the pin tips can be changed so as to minimize the bending moment applied to the pin bodies. That is the effective length of the pins is kept short so that the bending moment that is applied thereto is minimized.

Preferably the second ends of the arms are formed by enlarged circular end terminations each having generally radially extending serrations, the serrations of the first arm mating with the serrations of the second arm. Fastening means, such as a bolt of MRI and biologically compatible and CT transparent material, passes through a central opening in the enlarged end terminations, and is held in place by a nut of similar material. An arcuate elongated opening is provided in each of the arms at a portion thereof remote from the first ends of the arms, which is adapted to receive the strand which is used for applying the traction force to the tongs. The pins preferably include torque limiting caps for applying torque, such as shown in U.S. Pat. No. 4,838,264, the disclosure of which is hereby incorporated by reference herein.

The tongs and pins according to the present invention are preferably packaged in sterile packaging, and need only be used for one patient. That is, after they are removed from the sterile packaging and used in association with one patient, they may be thrown away. This is so because while the material utilized in the construction of the tongs is CT transparent, etc., it is relatively inexpensive (compared to stainless steel and titanium), and while it is capable of sterilization, it is most suitably not sterilized for reused.

According to another aspect of the present invention, a method of treating a human with an injury to the cervical spine is provided, the method comprising the steps of: (a) Adjusting the spacing between the pin tips by adjusting the relative angular position of the curved arms so as to conform to the skull width so that minimal bending moment is applied to the skull pins. (b) Holding the arms together in the desired position to which they have been angularly adjusted. (c) By applying torque to the skull pins, causing the pointed tips thereof to penetrate the skin of the human and engage the outer table of the human's skull. (d) Applying tension to the human's cervical spine by applying a force to the tongs. And, (e) without disturbing the tongs, CT scanning or magnetic resonance imaging the patient's skull. Step (a) is typically practiced by moving the serrations on the end terminations of the arms until the desired serrations for providing the desired spacing between the skull pins cooperate, and then fastening the end terminations together in that position. Step (c) is preferably practiced by rotating the torque limiting caps, the tong arms having sufficient elasticity to provide constant pressure urging the pointed pin tips against the patient's skull.

It is the primary object of the present invention to provide an advantageous cervical traction tong, and method of utilization thereof. This and other objects of the invention will become clear from an inspection of the detailed description of the invention, and from the appended claims.

BRIEF DESCRIPTION OF THE DRAWINGS

FIG. 1 is a end view of exemplary cervical traction tongs according to the invention;

FIG. 2 is a perspective view of the left arm of the tongs of FIG. 1;

FIG. 3 is a perspective view of a lock nut for mounting the pins in the arms of the tongs of FIG. 1;

FIG. 4 is a perspective exploded view of an exemplary pin, and pointed pin tip, of the tongs of FIG. 1; and FIG. 5 is a side view of a fastening device utilized to hold the tong arms in a position to which they have been adjusted.

DETAILED DESCRIPTION OF THE DRAWINGS

Cervical traction tongs according to the present invention are shown generally by reference numeral 10 in FIG. 1. Two of the major components of the tongs 10 comprise a first curved arm 11, and a second curved arm 12. The arms 11, 12 preferably are identical. The first arm 11 has a first end 13 and a second end 14 (FIG. 2), and is made out of an MRI and biologically compatible and CT transparent material, preferably a plastic. A wide variety of different plastics are suitable, and the selection of the particular type of plastic will depend upon many different criteria including whether or not the tongs are to be disposable, local availability, etc. Three examples of plastics that are suitable are: glass filled (e.g. 35%) ULTEM (a trademark of General Electric) polyesteramide, or glass or carbon fiber filled polysulfone, or fiber reinforced tempered nylon. The arm 11 preferably is an integral piece of plastic, such as made by injection molding.

At the first end 13 of the arm 11, means are provided for the receipt of a skull pin body so that the pin extends through the arms with the pin tip pointing toward the other arm 12. As shown in FIG. 2, such means preferably comprise a contoured through extending opening 16 which is adapted to receive a pin lock 17 (see FIG. 3) therein. The pin lock 17 has surface manifestations 18 which cooperate With corresponding surface manifestations in the contoured opening 16, and are positively held in place. An interior opening 19 extending through the center of the pin lock 17 is threaded, to cooperate with threads on the exterior of a pin to be received thereby. The material of the pin lock 17 is also MRI and biologically compatible and CT transparent, such as ULTEM 2200 plastic by G.E.

One form that a pin may take according to the present invention is illustrated generally by reference numeral 22 in FIG. 4. The pin 22 includes a main plastic pin body 23 having external threading 24 thereon. The pin body 23 passes through the central opening 19 in the pin lock 17, the threads between the two engaging. At one end of the pin body 23 a torque limiting knob 25 is provided, the knob and pin having the construction such as shown in U.S. Pat. No. 4,838,264, which has been incorporated by reference herein. At the other end of the pin body 23, a pointed skull pin tip 26 is provided. It is necessary that the tip 26 may be made of material that will effectively penetrate the skin and engage the outer table of the bone without deformation or breaking. At the time of this invention, no plastics are known which will accomplish that desired function, therefore the tip 26 is not itself entirely of CT transparent material. However preferably it is of radiolucent material, such as single crystal alumina ceramic as shown in U.S. Pat. No. 4,612,930, the disclosure of which has been incorporated by reference herein. Being radiolucent, the pin tips 26 result in minimal artifact in resultant films, so that there is no interference with diagnosis.

Because the pin body 23 is made of a plastic (e.g. boron or carbon fiber reinforced plastic and/or the same plastic as the arm 11), it does not have the strength of conventional titanium or stainless steel pins. Therefore care must be taken to ensure that there is not too long a length of pin body 23 extending inwardly from the arm 11. For this purpose, the arms 11, 12 are constructed so that they may have the relative positions thereof adjusted, to accommodate skulls of different width. In that way the bending moment to be applied to the skull pin may be minimized.

In order to provide for relative adjustment between the arms 11, 12, the arm 11 has formed at the second end 14 thereof an enlarged end termination 30, which preferably is circular, extending about 360° (although other constructions of lesser arcuate extent can be provided), and which has a plurality of serrations 31 which extend radially. Formed in the serrations at a portion thereof remote from the first end 13 is an arcuate elongated opening 33 which is adapted to receive a flexible strand 34 (see FIG. 1), such as a cable, which is ultimately connected up to the traction applying elements (e.g. weights).

The second arm 12 is preferably identical to the first arm 11, and the serrations thereof cooperate with the serrations 31 of the arm 11 to position the arms 11, 12 in a desired angular position, corresponding to the spacing (width) 36 between the pin tips 26 (see FIG. 1).

In order to hold the enlarged end terminations 30 into the relative angular position to which they have been moved, fastening means are provided. Preferably, a central through extending opening 38 is provided in each of the end terminations 30 of the arms 11, 12, and a bolt 39 (see FIG. 5 and FIG. 1) passes through the openings 38. The bolt 39, which is also of an MRI and biologically compatible and CT transparent material, such as ULTEM 2200 plastic by G.E., has a shaft 41, a head 42 with an internal hex 43 at one end thereof, and an exterior screw threading 44 at the other end thereof. The exterior screw threading 44 cooperates with an interiorly threaded nut 45 of the same material. In this way, the bolt 39 and nut 45 clamp the end terminations 30 together so that the desired serrations 31 thereof engage to hold the arms 11, 12 in the desired position depending upon the width of the person's skull.

Note that because of the arcuately elongated nature of the openings 33 in the end terminations 30, even though the angular position between the arms 11, 12 may change, the strand 34 may be properly received thereby. There is no need for providing for a large angular adjustment between the arms 11, 12, rather they need only be relatively arcuately adjustable about 15° in order to provide the appropriate adjustable spacing 36 between the pointed pin tips 26.

In utilizing the tongs 10, the patient's skull width is measured, and—with the bolt 39 and nut 45 loose—the end terminations 30 of the arms 11, 12 are angularly moved with respect to each other until the desired serrations 31 thereof cooperate for the position in which the width—spacing 36 between the pin tips 26—corresponds approximately to the width of the patient's skull. At this position, the bolt 39 and nut 45 are tightened, which holds the mating serrations 31 of the arms 11, 12 together to positively maintain the desired angular position between the arms 11, 12.

The tongs 10 are then placed around the patient's skull; at this juncture the tips 26 just barely in contact with the patient's skin. Then, by rotating the torque limiting knobs 25, the pins 26 are caused to penetrate the skin and engage the outer table of the patient's skull bone. This action must be sufficient so that the pins 26 are positively in place. The pin tips 26 are positively held in this position by the inherent elasticity of the arms 11, 12, no spring loading of the pins 23 being necessary, nor any force application to the arm articulations. The strand 34 is placed through the opening 33, and is connected up to the cervical traction applying mechanism, tension being applied to the human patient's cervical spine by applying a force to the tongs 10 through the strand 34.

Without disturbing the tongs 10, the patient may then have a CT scan or magnetic resonance imaging of his/her skull to assess brain condition (e.g. damage). Because of the MRI compatibility and CT transparency of the components of the tongs 10, it is not necessary to disturb the tongs to run MRI or CT procedures, yet diagnosis is straight-forward since there are no artifacts which interfere with diagnosis. The patient may be periodically subjected to any number of scans or imagings.

Preferably all of the components of the tongs 10—including the arms 11, 12, the pins 23 and tips 26, the pin lock 17, and the bolt 39 and nut 45 —are packaged in sterile packages. For example they could be all packaged together in the same kit, or could be packaged separately by component. Once the tong components are removed from the sterile packaging, they are used with a single patient, and once it is determined that the patient no longer need be in traction, the tongs may be disposed of, i.e. not reused.

It will thus be seen that according to the present invention, an apparatus and method have been provided for practicing effective cervical traction. While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent structures and processes.

WHAT IS CLAIMED IS:

1. Cervical traction tongs comprising:
   a first curved arm having first and second ends;
   a second curved arm having first and second ends;
   said arms of MRI and biologically compatible and CT transparent material;
   pins having main bodies of MRI and biologically compatible and CT transparent material and having pointed, skull engaging tips of biologically compatible and minimally artifacting material, associated with said arms;
   means formed at the first ends of said arms for receipt of said bodies of said pins, so that said pins extend through said arms with said tips pointing in a given dimension; and
   means formed at the second ends of each of said arms for cooperation with the other of said arms so that the relative angular position of said arms may be adjusted yet the arms are positively held in place in the position to which they are adjusted with the pin tips generally facing each other, so that the spacing between said pin tips can be changed so as to minimize the bending moment applied to said pin bodies.

2. Tongs as recited in claim 1 wherein said arms have sufficient elasticity to provide constant pressure urging the pointed pin tips against a skull during use.

3. Tongs as recited in claim 2 wherein said pin main bodies and said arms are made of plastic.

4. Tongs as recited in claim 3 further comprising torque limiting caps associated with said pin main bodies for applying torque.

5. Tongs as recited in claim 1 further comprising, at said second ends of said arms, means for receipt of a flexible strand which is adapted to be connected to a source of tension to be applied to the tongs.

6. Tongs as recited in claim 1 wherein said tips are of radiolucent material.

7. Tongs as recited in claim 6 wherein said tips are of single crystal alumina ceramic.

8. Tongs as recited in claim 1 wherein said means at said arm second ends for allowing relative angular adjustment therebetween comprises an enlarged end termination of each of said arms having generally radially extending serrations, the serrations of said first arm mating with the serrations of said second arm; and fastening means for holding said enlarged end terminations together with the serrations thereof cooperating so that relative movement between the enlarged end terminations is prevented.

9. Tongs as recited in claim 8 wherein said fastening means comprises means defining a through extending opening in each of said end terminations, a bolt of MRI and biologically compatible and CT transparent material extending through said openings in said end terminations, and a nut for engaging said bolt.

10. Tongs as recited in claim 8 wherein said end terminations are circular in plan view, said serrations being disposed 360° around said end terminations.

11. Tongs as recited in claim 10 wherein said means for receipt of a flexible strand comprises means defining cooperating arcuate, elongated, openings in said end terminations at portions thereof remote from said arm first ends.

12. Tongs as recited in claim 1 further comprising torque limiting caps associated with said pin main bodies for applying torque.

13. Tong as recited in claim 1 wherein said second arm is identical to said first arm.

14. A method of treating a human with an injury to the cervical spine, the human having a skull of a predetermined width, comprising the steps of:
   (a) utilizing tongs primarily of MRI and biologically compatible and CT transparent material with any portions thereof not radio transparent resulting in minimal artifact, and having plastic skull pins with pointed pin tips mounted on first and second angularly adjustable curved arms;
   (b) adjusting the spacing between the pin tips by adjusting the relative angular position of the curved arms so as to conform to the skull width so that minimal bending moment is applied to the skull pins;
   (c) holding the arms together in the desired position to which they have been angularly adjusted;
   (d) by applying torque to the skull pins, causing the pointed tips thereof to penetrate the skin of the human and engage the outer table of the human's skull;
   (e) applying tension to the human's cervical spine by applying a force to the tongs; and (f) without disturbing the tongs, CT scanning or magnetic resonance imaging the patient's skull.

15. A method as recited in claim 14 wherein the tongs arms have enlarged circular end terminations at a first end of each, having radially extending, cooperating serrations; and wherein step (a) is practiced by moving the serrations until the desired serrations for providing the desired spacing between the skull pins cooperate, and step (b) is practiced by fastening the end terminations together with the desired serrations cooperating.

16. A method as recited in claim 14 wherein the skull pins have torque limiting caps, and wherein step (c) is practiced by rotating the torque limiting caps.

17. A method as recited in claim 14 wherein the tongs and skull pins are provided in sterile packaging, and comprising the further step, prior to step (a), of removing the tongs and skull pins from the sterile packaging; and wherein step (e) is repeated, if necessary, until it is determined that the human need no longer remain in traction; and comprising the further step, after it is determined that the human need no longer remain in traction, of disposing of the tongs and skull pins so that they are not reused.

18. Cervical traction tongs comprising:

a first arm having first and second ends;

said first end having means defining a skull pin receiving opening having a first axis;

said second end having an enlarged circular end termination having a plurality of radially extending serrations, with means defining a central opening in said serrations, said central opening having a second axis;

means defining an arcuately elongated opening in said serrations at a portion thereof remote from said first end, said elongated opening for receipt of a flexible tension applying strand;

a second arm identical to said first arm, with the serrations thereof cooperating with the serrations of said first arm;

fastening means extending through said central openings for fastening said arms together at a predetermined position at which said serrations cooperate;

the second axes of said arms disposed in a plane perpendicular to said first axis;

a skull pin extending through each of said openings in said arm first ends, and having a pointed tip facing the other arm; and said arms having sufficient elasticity so as to apply constant pressure on said pointed tips of said skull pins when they engage a human skull.

19. Tongs as recited in claim 18 wherein said pins and arms are made of an MRI and biologically compatible and CT transparent plastic, and wherein said pointed tips of said pins are of a material that minimally artifacts.

20. Tongs as recited in claim 19 wherein said pointed tips of said pins are made of single crystal alumina ceramic.

* * * * *